US009399663B2

(12) United States Patent
Mocchetti et al.

(10) Patent No.: US 9,399,663 B2
(45) Date of Patent: Jul. 26, 2016

(54) COMPETITIVE INHIBITOR OF GP120

(71) Applicant: GEORGETOWN UNIVERSITY, Washington, DC (US)

(72) Inventors: Italo Mocchetti, Potomac, MD (US); Valeriya Avdoshina, Fairfax, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 14/630,246

(22) Filed: Feb. 24, 2015

(65) Prior Publication Data

US 2015/0239933 A1 Aug. 27, 2015

Related U.S. Application Data

(60) Provisional application No. 61/943,711, filed on Feb. 24, 2014.

(51) Int. Cl.

| | |
|---|---|
| ***C07K 7/08*** | (2006.01) |
| ***C07K 14/00*** | (2006.01) |
| ***C07K 14/16*** | (2006.01) |
| *A61K 38/00* | (2006.01) |

(52) U.S. Cl.
CPC . *C07K 7/08* (2013.01); *C07K 14/00* (2013.01); *C07K 14/162* (2013.01); *A61K 38/00* (2013.01)

(58) Field of Classification Search
None
See application file for complete search history.

(56) References Cited

FOREIGN PATENT DOCUMENTS

EP 0273716 * 7/1988 ............... C07K 7/08

OTHER PUBLICATIONS

Porta et al. Peptide modified mesoporous silica nanocontainers. Phys. Chem. Chem. Phys., 2011, 13, 9982-9985.*

* cited by examiner

*Primary Examiner* — Satyanarayana R Gudibande
*Assistant Examiner* — Jia-Hai Lee
(74) *Attorney, Agent, or Firm* — Womble Carlyle Sandridge & Rice, LLP

(57) ABSTRACT

Peptides and peptide analogs that competitively inhibit HIV protein gp120 and methods for making and using the same.

3 Claims, 11 Drawing Sheets

SEQUENCE LISTING

```
<160> NUMBER OF SEQ ID NOS: 15

<210> SEQ ID NO 1
<211> LENGTH: 20
<212> TYPE: PRT
<213> ORGANISM: Artificial Sequence
<220> FEATURE:
<223> OTHER INFORMATION: Synthetic peptide

<400> SEQUENCE: 1

Asn Asp Met Val Glu Gln Met His Glu Asp Ile Ile Ser Leu Trp Asp
1               5                   10                  15

Gln Ser Leu Lys
            20


<210> SEQ ID NO 2
```

<211> LENGTH: 36
<212> TYPE: PRT
<213> ORGANISM: Artificial Sequence
<220> FEATURE:
<223> OTHER INFORMATION: Synthetic peptide

<400> SEQUENCE: 2

```
Arg Gln Ile Lys Ile Trp Phe Gln Asn Arg Arg Met Lys Trp Lys Lys
1               5                   10                  15

Asn Asp Met Val Glu Gln Met His Glu Asp Ile Ile Ser Leu Trp Asp
            20                  25                  30

Gln Ser Leu Lys
        35
```

<210> SEQ ID NO 3
<211> LENGTH: 11
<212> TYPE: PRT
<213> ORGANISM: Homo sapiens

<400> SEQUENCE: 3

```
Glu Gly Glu Gly Glu Glu Glu Gly Glu Glu Tyr
1               5                   10
```

<210> SEQ ID NO 4
<211> LENGTH: 10
<212> TYPE: PRT
<213> ORGANISM: Homo sapiens

<400> SEQUENCE: 4

```
Glu Gly Glu Gly Glu Glu Glu Gly Glu Glu
1               5                   10
```

<210> SEQ ID NO 5
<211> LENGTH: 9
<212> TYPE: PRT
<213> ORGANISM: Homo sapiens

<400> SEQUENCE: 5

```
Glu Gly Glu Gly Glu Glu Glu Gly Glu
1               5
```

<210> SEQ ID NO 6
<211> LENGTH: 10
<212> TYPE: PRT
<213> ORGANISM: Homo sapiens

<400> SEQUENCE: 6

```
Glu Gly Glu Gly Glu Glu Glu Gly Gln Gln
1               5                   10
```

<210> SEQ ID NO 7
<211> LENGTH: 11
<212> TYPE: PRT
<213> ORGANISM: Homo sapiens

-continued

<400> SEQUENCE: 7

Glu Gly Glu Gly Glu Glu Glu Gly Gln Gln Gln
1               5                   10

<210> SEQ ID NO 8
<211> LENGTH: 12
<212> TYPE: PRT
<213> ORGANISM: Homo sapiens

<400> SEQUENCE: 8

Glu Gly Glu Gly Glu Glu Glu Gly Gln Gln Gln Gln
1               5                   10

<210> SEQ ID NO 9
<211> LENGTH: 9
<212> TYPE: PRT
<213> ORGANISM: Homo sapiens

<400> SEQUENCE: 9

Glu Asp Glu Asp Glu Gly Glu Glu Tyr
1               5

<210> SEQ ID NO 10
<211> LENGTH: 8
<212> TYPE: PRT
<213> ORGANISM: Homo sapiens

<400> SEQUENCE: 10

Glu Asp Glu Asp Glu Gly Glu Glu
1               5

<210> SEQ ID NO 11
<211> LENGTH: 7
<212> TYPE: PRT
<213> ORGANISM: Homo sapiens

<400> SEQUENCE: 11

Glu Asp Glu Asp Glu Gly Glu
1               5

<210> SEQ ID NO 12
<211> LENGTH: 9
<212> TYPE: PRT
<213> ORGANISM: Homo sapiens

<400> SEQUENCE: 12

Glu Glu Glu Glu Gly Glu Asp Glu Ala
1               5

<210> SEQ ID NO 13
<211> LENGTH: 9
<212> TYPE: PRT
<213> ORGANISM: Homo sapiens

<400> SEQUENCE: 13

Glu Asp Asp Glu Glu Glu Ser Glu Ala
1               5

<210> SEQ ID NO 14
<211> LENGTH: 14
<212> TYPE: PRT
<213> ORGANISM: Homo sapiens

<400> SEQUENCE: 14

-continued

```
Arg Ala Lys Trp Asn Asn Thr Leu Lys Gln Ile Ala Ser Lys
1               5                   10


<210> SEQ ID NO 15
<211> LENGTH: 14
<212> TYPE: PRT
<213> ORGANISM: Homo sapiens

<400> SEQUENCE: 15

Asn Ser Ser Tyr Phe Val Glu Trp Ile Pro Asn Asn Val Lys
1               5                   10
```

COMPETITIVE INHIBITOR OF GP120

CROSS-REFERENCE TO RELATED APPLICATIONS

This application claims priority to U.S. Provisional Patent Application No. 61/943,711, filed 24 Feb. 2014.

STATEMENT REGARDING FEDERALLY SPONSORED RESEARCH OR DEVELOPMENT

This invention was made with government support under Grants 1R21 NS074916 and 1R01 NS079172-01A1 awarded by the National Institute of Neurological Disorders and Stroke. The government has certain rights in inventions disclosed herein.

INCORPORATION BY REFERENCE TO SEQUENCE LISTING

A text file of the Sequence Listing named "SEQL.txt" is submitted herewith and incorporated by reference in its entirety. The Sequence Listing was created on 24 Feb. 2015, is 2.97 kB in size, and discloses SEQ ID NOs: 1-15 described herein.

TECHNICAL FIELD OF THE INVENTION

The invention relates generally to peptides and peptide mimetics that competitively inhibit the HIV protein gp-120, as well as methods for making and using the same to prevent and/or ameliorate HIV-mediated neurodegeneration and HIV-associated dementia (HAD).

BACKGROUND OF THE INVENTION

HIV enters the central nervous system (CNS) very early after seroconversion. However, synaptic simplification, seen in HW-positive subjects, occurs in the late stage of infection. These abnormalities culminate in neurocognitive deficits termed HIV-associated neurocognitive disorder (HAND) or, the more severe form, HIV-associated dementia, even in the presence of the antiretroviral therapy. Symptoms include profound motor and behavioral/psychosocial abnormalities that negatively influence daily living.

Remarkably, HIV does not infect neurons, yet postmortem brains of subjects with HAD exhibit neuronal loss accompanied by synaptic simplification. Neurodegeneration seen in HIV positive subjects has been attributed to the combined effect of host cell-derived factors, including cytokines and glutamate and other neurotoxins produced by activated microglia/macrophages. In fact, HIV infection causes HIV encephalitis, which is characterized by neuroinflammation, astrogliosis and microgliosis, and results in an overall production and release of pro-apoptotic chemokines (e.g., interleukin-1β and tumor necrosis factor-α). However it is still unclear whether HIV, through viral proteins, can induce neuronal damage directly.

There are presently no therapies available for treating HAD. Thus, there is an acute need for developing adjunct therapies that can provide some measure of treating HIV-mediated neuronal degeneration.

BRIEF SUMMARY OF THE INVENTION

The present invention relates to a competitive inhibitor of HIV protein gp-120, a peptide named Helix A gp120, recombinant polynucleotides encoding Helix A gp120, vectors and cells expressing Helix A gp120 polynucleotides, and Helix A gp120 peptide mimetics. Pharmaceutical compositions and formulations are also disclosed.

The present invention also relates to methods to treat and/or ameliorate HIV-mediated neurodegeneration and HIV-associated dementia (HAD) in a subject using Helix A gp120 peptides and pharmaceutical compositions comprising the same.

One embodiment of the invention encompasses a recombinant peptide comprising the sequence NDMVEQMHEDIISLWDQSLK (SEQ ID NO: 1). In an alternative embodiment, the recombinant peptide consists essentially of the sequence NDMVEQMHEDIISLWDQSLK (SEQ ID NO: 1). In yet another alternative embodiment, the recombinant peptide consists of the sequence NDMVEQMHEDIISLWDQSLK (SEQ ID NO: 1).

Another embodiment of the invention encompasses a recombinant peptide comprising the sequence RQIKIWFQNRRMKWKKNDMVEQMHEDIISLWDQSLK (SEQ ID NO: 2). In an alternative embodiment, the recombinant peptide consists essentially of the sequence RQIKIWFQNRRMKWKKNDMVEQMHEDIISLWDQSLK (SEQ ID NO: 2). In yet another alternative embodiment, the recombinant peptide consists of the sequence RQIKIWFQNRRMKWKKNDMVEQMHEDIISLWDQSLK (SEQ ID NO: 2).

Another embodiment of the invention encompasses a recombinant nucleic acid encoding a recombinant peptide comprising the sequence NDMVEQMHEDIISLWDQSLK (SEQ ID NO: 1). In an alternative embodiment, the recombinant nucleic acid encodes a recombinant peptide consisting essentially of the sequence NDMVEQMHEDIISLWDQSLK (SEQ ID NO: 1). In yet another alternative embodiment, the recombinant nucleic acid encodes a recombinant peptide consisting of the sequence NDMVEQMHEDIISLWDQSLK (SEQ ID NO: 1).

Another embodiment of the invention encompasses a recombinant nucleic acid encoding a recombinant peptide comprising the sequence RQIKIWFQNRRMKWKKNDMVEQMHEDIISLWDQSLK (SEQ ID NO: 2). In an alternative embodiment, the recombinant nucleic acid encodes a recombinant peptide consisting essentially of the sequence RQIKIWFQNRRMKWKKNDMVEQMHEDIISLWDQSLK (SEQ ID NO: 2). In yet another alternative embodiment, the recombinant nucleic acid encodes a recombinant peptide consisting of the sequence RQIKIWFQNRRMKWKKNDMVEQMHEDIISLWDQSLK (SEQ ID NO: 2).

Another embodiment of the invention encompasses a vector comprising the recombinant nucleic acids disclosed herein.

Another embodiment of the invention encompasses a host cell comprising the recombinant nucleic acids disclosed herein. In an alternative embodiment, the host cell comprises the vectors described herein.

Another embodiment of the invention encompasses pharmaceutical compositions comprising the recombinant peptides disclosed herein. In alternative embodiments, the pharmaceutical compositions, the recombinant peptide is crosslinked to a APTES-modified silica particle.

Another embodiment of the invention encompasses a method of therapeutically treating HIV-mediated neurodegeneration in a subject comprising administering one or more recombinant peptides and/or pharmaceutical compositions disclosed herein. It is contemplated that the one or more recombinant peptides and/or pharmaceutical compositions disclosed herein are administered in an amount and for a time sufficient to treat the HIV-mediated neurodegeneration.

Another embodiment of the invention encompasses a method of prophylactically treating HIV-mediated neurodegeneration in a subject comprising administering one or more recombinant peptides and/or pharmaceutical compositions disclosed herein. It is contemplated that the one or more recombinant peptides and/or pharmaceutical compositions disclosed herein are administered in an amount and for a a time sufficient to prevent or delay the onset of HIV-mediated neurodegeneration.

Another embodiment of the invention encompasses a method of therapeutically treating HIV-associated dementia (HAD) in a subject comprising administering one or more recombinant peptides and/or pharmaceutical compositions disclosed herein. It is contemplated that the one or more recombinant peptides and/or pharmaceutical compositions disclosed herein are administered in an amount and for a time sufficient to treat the HIV-mediated dementia.

Another embodiment of the invention encompasses a method of ameliorating HIV-associated dementia (HAD) in a subject comprising administering one or more recombinant peptides and/or pharmaceutical compositions disclosed herein. It is contemplated that the one or more recombinant peptides and/or pharmaceutical compositions disclosed herein are administered in an amount and for a time to prevent or delay the onset of HIV-mediated dementia.

Another embodiment of the invention encompasses a method of preventing or delaying the onset of gp120-induced neurotoxicity comprising administering one or more recombinant peptides and/or pharmaceutical compositions disclosed herein. It is contemplated that the one or more recombinant peptides and/or pharmaceutical compositions disclosed herein are administered in an amount and for a time to prevent or delay the onset of gp120-induced neurotoxicity.

Another embodiment of the invention encompasses a method of preventing or delaying the onset of gp120-mediated neurite pruning comprising administering one or more recombinant peptides and/or pharmaceutical compositions disclosed herein. It is contemplated that the one or more recombinant peptides and/or pharmaceutical compositions disclosed herein are administered in an amount and for a time to prevent or delay the onset of gp120-mediated neurite pruning.

Another embodiment of the invention encompasses a method of preventing or delaying the onset of gp120-induced neuronal loss comprising administering one or more recombinant peptides and/or pharmaceutical compositions disclosed herein. It is contemplated that the one or more recombinant peptides and/or pharmaceutical compositions disclosed herein are administered in an amount and for a time to prevent or delay the onset of gp120-induced neuronal loss.

Another embodiment of the invention encompasses a method of preventing or delaying the onset of gp120-related mitochondrial morphological abnormalities comprising administering one or more recombinant peptides and/or pharmaceutical compositions disclosed herein. It is contemplated that the one or more recombinant peptides and/or pharmaceutical compositions disclosed herein are administered in an amount and for a time to prevent or delay the onset of gp120-related mitochondrial morphological abnormalities.

DETAILED DESCRIPTION OF THE INVENTION

Figure 1:
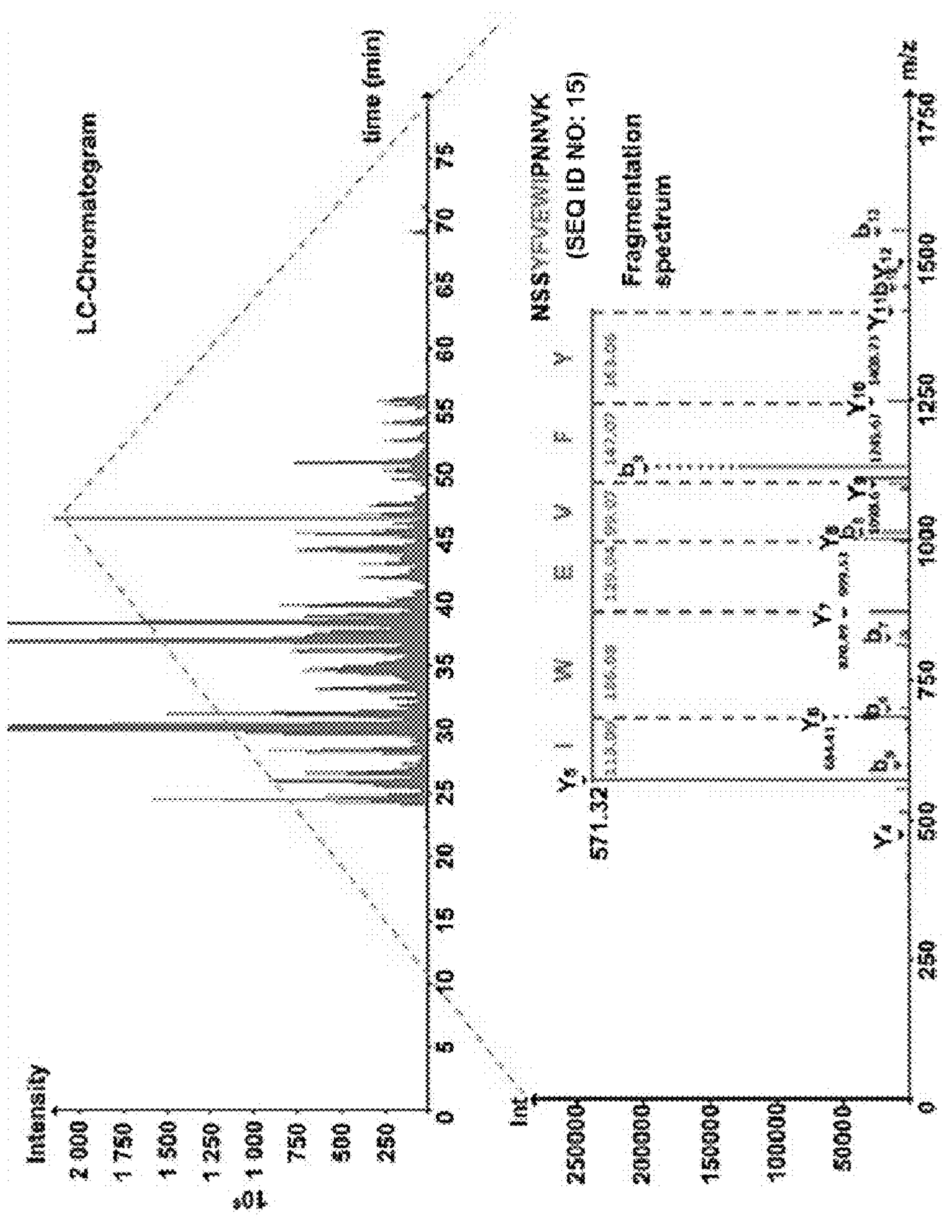
FIG. 1 shows high-performance liquid chromatography with tandem mass spectrometry (LC-MS/MS) analysis of lysates from gp120-treated neurons. LC-MS/MS analysis identifies tubulin β-3 (TUBB3) as an interactor of gp120IIIB Top panel: Chromatogram of the whole data set of gp120 interactors. In orange is indicated the peak (retention time=46.45 minutes) associated to peptide $^{337}$NSSYFVEWIPNNVK$^{350}$ (SEQ ID NO: 15) of TUBB3. Bottom panel: The fragmentation spectrum of peptide [337-350] of TUBB3 is shown to identify TUBB3 among gp120IIIB interactors. The series of y sequence coverage is highlighted.
Figure 2:
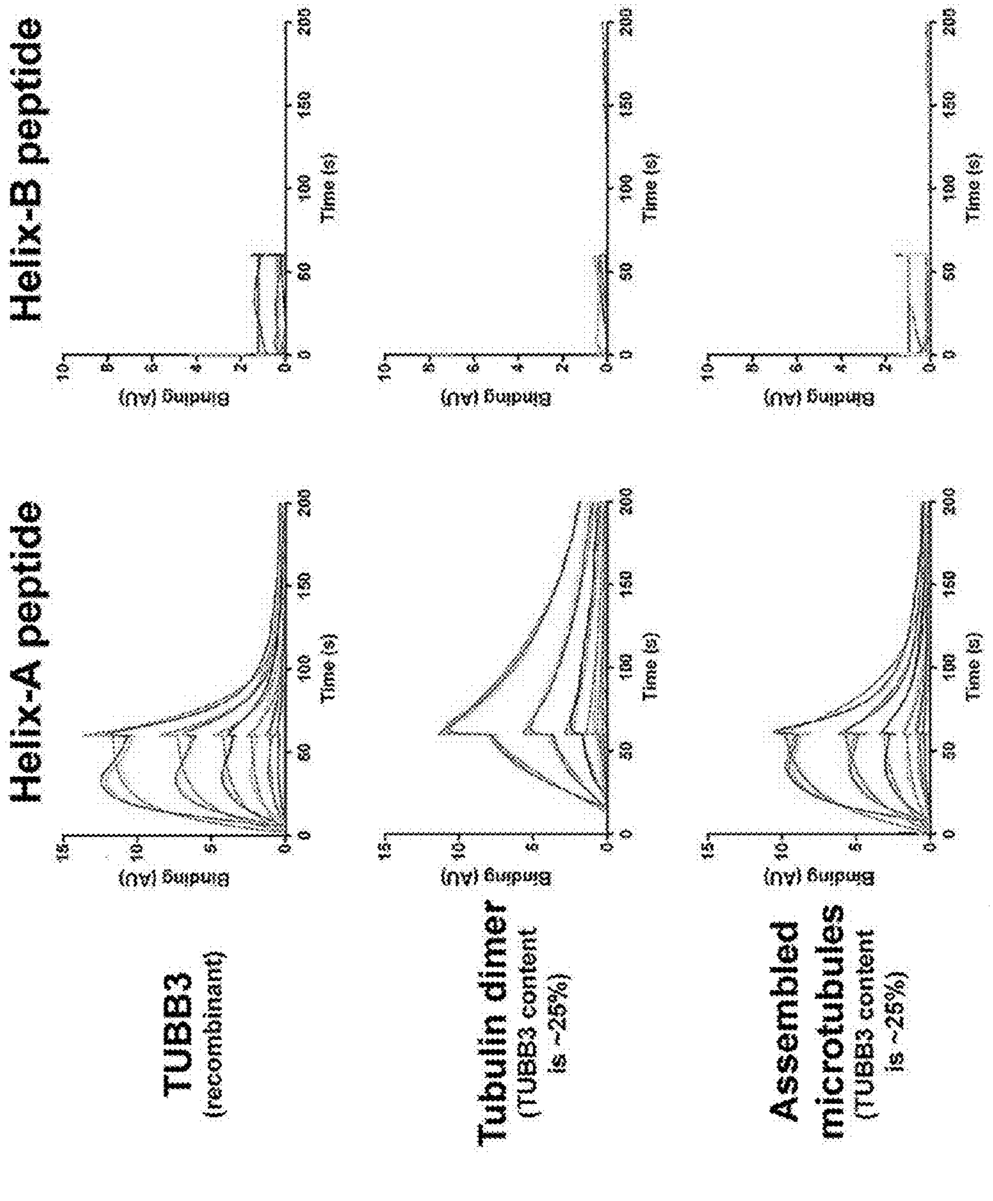
FIG. 2 shows the binding affinity of Helix peptides to tubulin. Representative sensorgrams of the binding of Helix-A and Helix-B peptides to TUBB3, tubulin dimer, and assembled microtubules (MTs). Color denotes the concentration of Helix-peptides used (purple=20 μM, green=10 μM, blue=5 μM, yellow=2.5 μM, emerald=1250 nM, and red=625 nM). Each concentration was injected three times over the sensor surface. The kinetics of interaction was analyzed using Biacore T200 instrument. BiaEvaluation software was used to calculate binding affinities based on 1:1 binding model.
Figure 3:
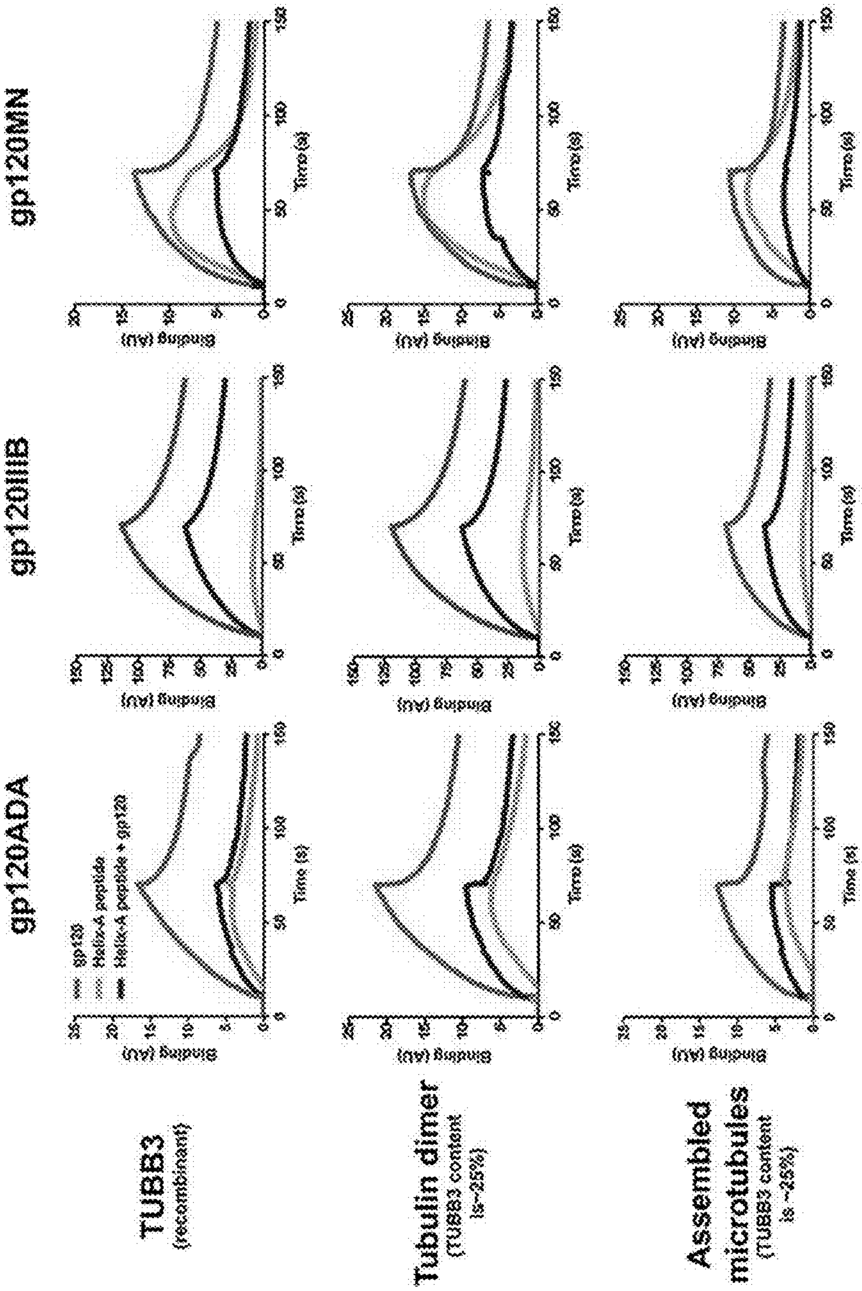
FIG. 3 shows that Helix-A peptide competes for gp120s binding to TUBB3, tubulin dimer, and assembled MTs. BIACORE® T200™ was used to determine the kinetic parameters for the binding of recombinant TUBB3, tubulin dimer, and assembled MTs to gp120s in the absence and presence of Helix-A peptide. Gp120s (100 nM) were injected over the surface alone or as a premix with Helix-A peptides (10 μM). Representative data are from one of three independent experiments.
Figure 4:
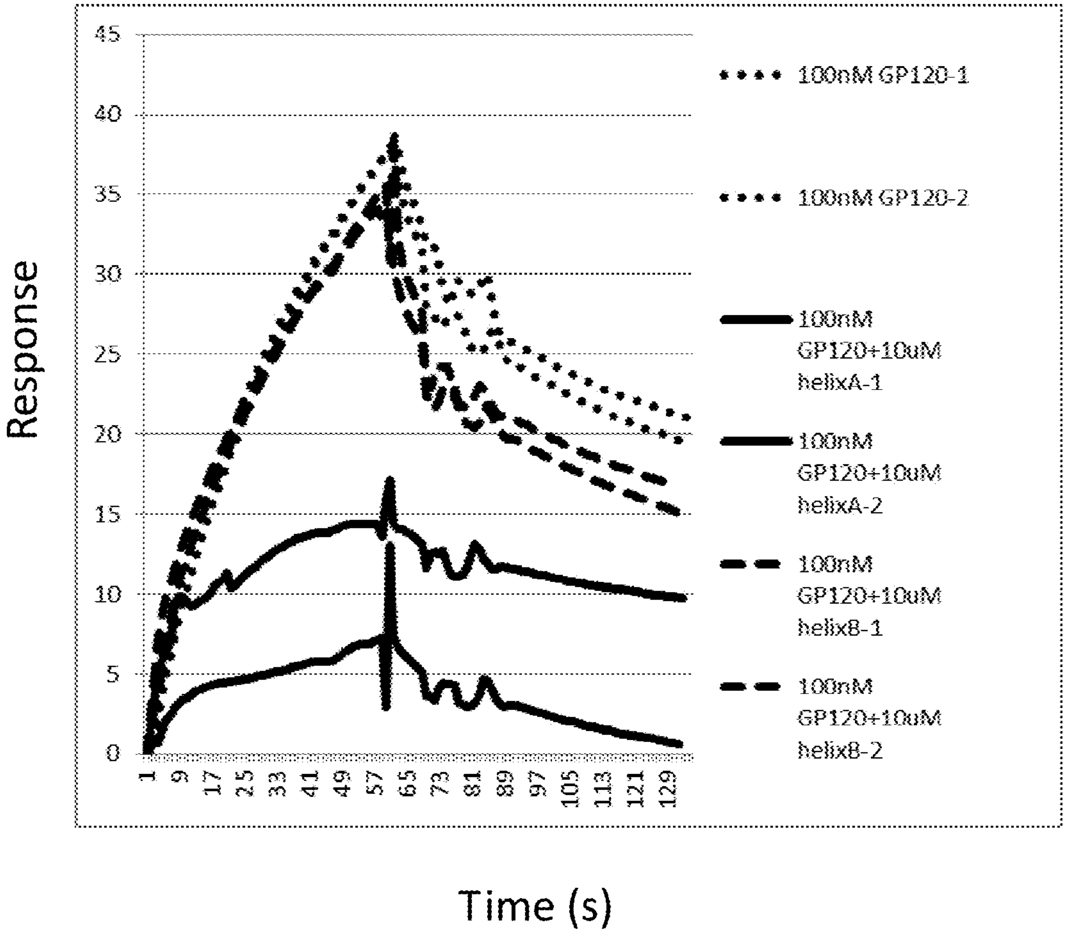
FIG. 4 shows that Helix A prevents gp120IIIB from binding to tubulin β-3.
Figure 5:
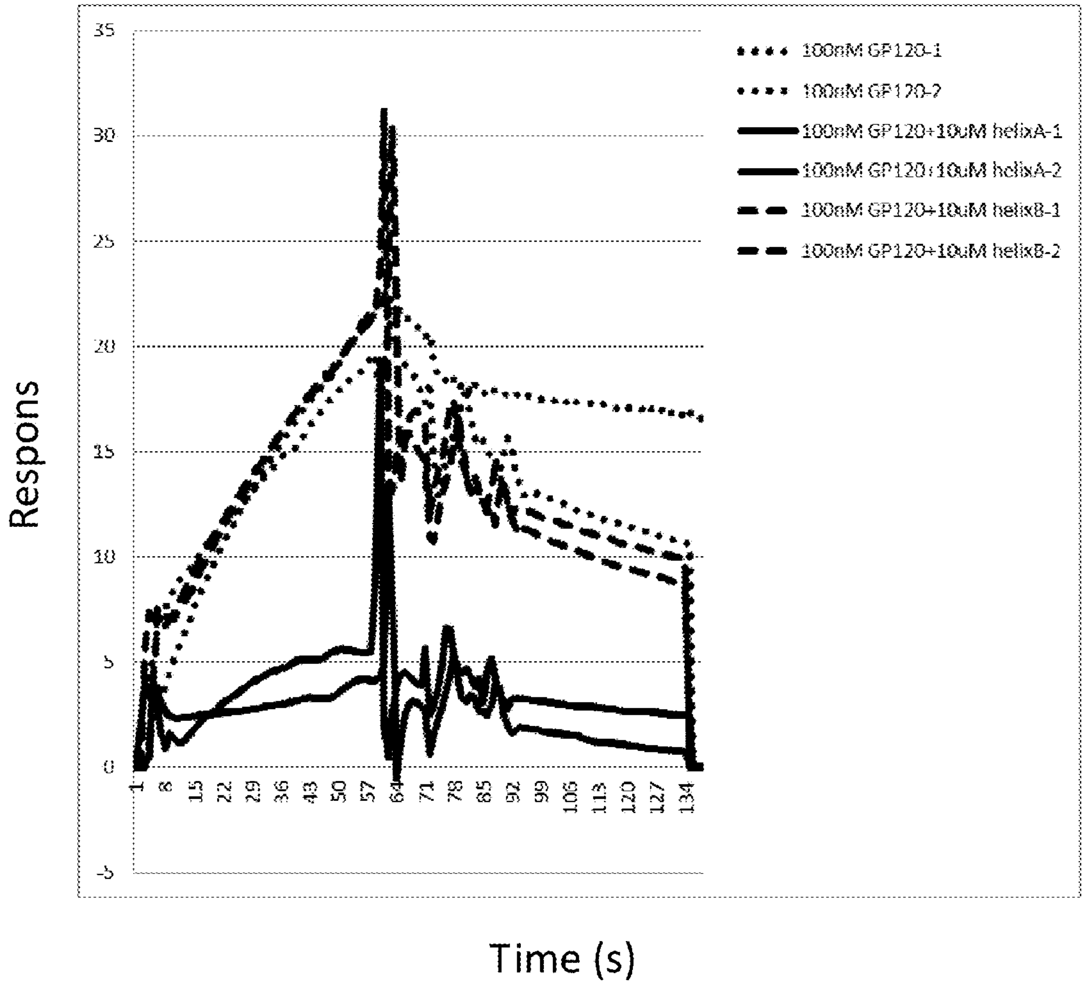
FIG. 5 shows that Helix A prevents gp120IIIB from binding to the tubulin dimer.

Helix A gp120 Peptides and Peptide Mimetics

The present invention relates to a competitive inhibitor of HIV protein gp-120, a peptide named Helix A gp120 and related variants. As used herein, the term "peptide" and plural variants refer to a compound made up of a single chain of amino acids joined by peptide bonds. Helix A gp120 peptides may comprise naturally occurring amino acids, synthetic amino acids, genetically encoded amino acids, non-genetically encoded amino acids, conservative amino-acid substitutions and combinations thereof. Peptides may include both L-form and D-form amino acids and may be optimized as described hereinafter. Exemplary Helix A gp120 peptides in accordance with the invention include NDMVEQMHEDIISLWDQSLK (SEQ ID NO: 1) and RQIKIWFQNRRMKWKKNDMVEQMHEDIISLWDQSLK (SEQ ID NO: 2).

Representative synthetic amino acids include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Methods of chemically synthesizing peptides comprising any of the foregoing types of amino acids are known to one of ordinary skill in the art (e.g., solid-phase peptide synthesis).

Representative non-genetically encoded amino acids include but are not limited to 2-aminoadipic acid; 3-aminoadipic acid; β-aminopropionic acid; 2-aminobutyric acid; 4-aminobutyric acid (piperidinic acid); 6-aminocaproic acid; 2-aminoheptanoic acid; 2-aminoisobutyric acid; 3-aminoisobutyric acid; 2-aminopimelic acid; 2,4-diaminobutyric acid; desmosine; 2,2'-diaminopimelic acid; 2,3-diaminopropionic acid; N-ethylglycine; N-ethylasparagine; hydroxylysine; allo-hydroxylysine; 3-hydroxyproline; 4-hydroxyproline; isodesmosine; allo-isoleucine; N-methylglycine (sarcosine); N-methylisoleucine; N-methylvaline; norvaline; norleucine; and ornithine.

Naturally occurring amino acids may be conservatively substituted for one another. Conservative substitutions involve substitutions between amino acids in the same group. Group I (Ala, Ile, Leu, Met and Val) consists of amino acids with hydrophobic side chains. Group II (Cys, Ser and Thr) consists of amino acids with neutral hydrophilic side chains. Group III (Asp and Glu) consists of amino acids with acidic side chains. Group IV (Arg, Asn, Gln, His and Lys) consists of amino acids with basic side chains. Group V (Gly and Pro) consists of amino acids with residues influencing chain orientation. Finally, Group VI (Phe, Trp and Tyr) consists of amino acids with aromatic side chains.

Helix A gp120 peptides may also be optimized by synthesizing them in a way that increases their stability, bioavailability and/or efficacy. In some embodiments, hydrophobic groups such as carbobenzoxyl, dansyl, or t-butyloxycarbonyl groups, may be added to the peptides' amino termini. In addition or alternatively, an acetyl group or a 9-fluorenylmethoxy-carbonyl group may be placed at the peptides' amino termini. In other embodiments, the bonds that link amino acid residues may be substituted by non-peptide bonds (e.g., imino, ester, hydrazide, semicarbazide, and azo bonds) utilizing reactions known in the art. Other contemplated modifications such as cyclization and retro-inversion are described in Mason, *Future Med. Chem.,* 2010, 2(12):1813-1822.

Helix A gp120 peptides may be purified, synthesized and/or characterized using a variety of standard techniques that are known to the skilled artisan (see e.g., Schroder et al., *The Peptides,* 1965, Academic Press, New York; Bodanszky, *Principles of Peptide Synthesis,* 2nd rev. ed. 1993, Springer-Verlag, Berlin/New York; Ausubel (ed.), *Short Protocols in Molecular Biology,* 3rd ed., 1995, Wiley, New York).

Helix A gp120 Nucleic Acids

As used herein, the terms "nucleic acid", "polynucleotide", "polynucleotide molecule", "polynucleotide sequence" and plural variants are used interchangeably to refer to a wide variety of molecules, including single strand and double strand DNA and RNA molecules, cDNA sequences, genomic DNA sequences of exons and introns, chemically synthesized DNA and RNA sequences, and sense strands and corresponding antisense strands. Polynucleotides of the invention may also comprise known analogs of natural nucleotides that have similar properties as the corresponding natural nucleic acid. Particularly contemplated are Helix A gp120 peptide cDNA degenerate coding sequences.

Polynucleotides of the present invention may be cloned, synthesized, altered, mutagenized, or combinations thereof. Standard recombinant DNA and molecular cloning techniques used to isolate nucleic acids are known in the art. Site-specific mutagenesis to create base pair changes, deletions, or small insertions is also known in the art (see e.g., Sambrook et al. (eds.) *Molecular Cloning: A Laboratory Manual,* 1989, Cold Spring Harbor Laboratory Press, Cold Spring Harbor, N.Y.; Silhavy et al., *Experiments with Gene Fusions,* 1984, Cold Spring Harbor Laboratory Press, Cold Spring Harbor, N.Y.; Glover & Hames, *DNA Cloning: A Practical Approach,* 2nd ed., 1995, IRL Press at Oxford University Press, Oxford/New York; Ausubel (ed.) *Short Protocols in Molecular Biology,* 3rd ed., 1995, Wiley, New York).

Helix A gp120 Expression Systems

An expression system refers to a host cell comprising a heterologous nucleic acid and the protein encoded by the heterologous nucleic acid. For example, a heterologous expression system may comprise a host cell transfected with a construct comprising a Helix A gp120 nucleic acid encoding a protein operatively linked to a promoter, or a cell line produced by introduction of Helix A gp120 nucleic acids into a host cell genome. The expression system may further comprise one or more additional heterologous nucleic acids relevant to Helix A gp120 function, such as targets of Helix A gp120 transcriptional activation or repression activity. These additional nucleic acids may be expressed as a single construct or multiple constructs.

A construct for expressing a Helix A gp120 protein may include a vector sequence and a Helix A gp120 nucleotide sequence, wherein the Helix A gp120 nucleotide sequence is operatively linked to a promoter sequence. A construct for recombinant Helix A gp120 expression may also comprise transcription termination signals and sequences required for proper translation of the nucleotide sequence. Constructs may also contain a ‘signal sequence’ or ‘leader sequence’ to facilitate co-translational or post-translational transport of the peptide of interest to certain intracellular structures such as the endoplasmic reticulum or Golgi apparatus. Constructs can also contain 5' and 3' untranslated regions. A 3' untranslated region is a polynucleotide located downstream of a coding sequence. Polyadenylation signal sequences and other sequences encoding regulatory signals capable of affecting the addition of polyadenylic acid tracts to the 3' end of the mRNA precursor are 3' untranslated regions. A 5' untranslated region is a polynucleotide located upstream of a coding sequence. Preparation of an expression construct, including addition of translation and termination signal sequences, is known to one skilled in the art.

The promoter may be any polynucleotide sequence that shows transcriptional activity in the host cell. The promoter may be native or analogous, or foreign or heterologous, to the host cell and/or to the DNA sequence of the invention. Where the promoter is native or endogenous to the host cell, it is intended that the promoter is found in the cell into which the promoter is introduced. Where the promoter is foreign or heterologous to the DNA sequence of the invention, the promoter is not the native or naturally occurring promoter for the operably linked DNA sequence of the invention. The promoter may be inducible or constitutive. It may be naturally-occurring, may be composed of portions of various naturally-occurring promoters, or may be partially or totally synthetic. Guidance for the design of promoters is provided by studies of promoter structure, such as that of Harley et al., *Nucleic Acids Res.,* 15:2343-61 (1987). Also, the location of the promoter relative to the transcription start may be optimized (see e.g., Roberts et al., *Proc. Natl. Acad. Sci. USA,* 76:760-4 (1979)). Many suitable promoters for use in human cell lines are well known in the art. The promoter may include, or be modified to include, one or more enhancer elements to thereby provide for higher levels of transcription. Where appropriate, the vector and Helix A gp120 sequences may be optimized for increased expression in the transformed host cell. That is, the sequences can be synthesized using host cell-preferred codons for improving expression, or may be synthesized using codons at a host-preferred codon usage frequency.

Host Cells

Host cells are cells into which a heterologous nucleic acid molecule of the invention may be introduced. A host cell line may be chosen which modulates the expression of the recombinant sequence, or modifies and processes the gene product in a specific manner. For example, different host cells have characteristic and specific mechanisms for the translational and post-translational processing and modification (e.g., glycosylation, phosphorylation of proteins). Appropriate cell lines or host cells may be chosen to ensure the desired modification and processing of the foreign protein expressed.

The present invention further encompasses recombinant expression of a Helix A gp120 protein or peptide in a stable cell line. Methods for generating a stable cell line following transformation of a heterologous construct into a host cell are known in the art (see e.g., Joyner, *Gene Targeting: A Practical Approach,* 1993, Oxford University Press, Oxford/New York). Thus, transformed cells and tissues are understood to encompass not only the end product of a transformation process, but also transgenic progeny or propagated forms thereof.

Pharmaceutical Compositions

Pharmaceutical compositions in accordance with the present invention comprise at least one Helix A gp120 peptide or a pharmaceutically acceptable derivative thereof. Pharmaceutical compositions in accordance with the present invention may optionally comprise one or more additional therapeutic agents that enhance or facilitate the treatment or amelioration of HAD or other anti-HIV agent (e.g., reverse transcriptase inhibitor, protease inhibitor, inhibitor of mRNA processing, inhibitor of protein glycosylation, or inhibitor of viral fusion. Such agents include but are not limited to nucleoside analogs or chain terminators (e.g., dideoxynucleosides)).

In a preferred pharmaceutical composition, Helix A gp120 peptides are cross-linked to 3-aminopropyltriethoxy silane (APTES) modified silica particles.

Pharmaceutical compositions in accordance with the present invention may be administered using techniques well known to those in the art. The pharmaceutical compositions may be formulated in conventional manner using one or more physiologically acceptable carriers comprising excipients and auxiliaries which facilitate processing of the active compounds into preparations which can be used pharmaceutically. Proper formulation is dependent upon the route of administration chosen. Preferably, the pharmaceutical compositions are formulated and administered systemically and may be in the form of a capsule, cream, dispersion, dragee, gel, patch, mini-pump, solution, suspension, suppository, syrup, tablet, troche, or the like. An exhaustive list of techniques for the formulation and administration of pharmaceutical compositions may be found in *Remington: The Science and Practice of Pharmacy,* $21^{st}$ Edition (Lippincott Williams & Wilkins, 2006).

Suitable routes of administration of the pharmaceutical compositions include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections; transdermal, topical, vaginal and the like.

Pharmaceutical compositions formulated for injection may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

Pharmaceutical compositions formulated for parenteral administration may be by way of bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing.

Pharmaceutical compositions formulated for parenteral administration also include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions formulated for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For oral administration, the pharmaceutical compositions can be formulated with pharmaceutically acceptable carriers well known in the art. Such carriers enable the pharmaceutical compositions to be formulated as tablets, pills, dragees, capsules, liquids, gels, syrups, slurries, suspensions and the like, for oral ingestion by a patient to be treated. The pharmaceutical compositions for oral administration can be formulated with solid excipients, optionally grinding a resulting mixture, and processing the mixture of granules, after adding suitable auxiliaries, if desired, to obtain tablets or dragee cores.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions formulated for buccal administration may take the form of tablets or lozenges formulated in conventional manner.

Pharmaceutical compositions formulated for administration by inhalation may be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Pharmaceutical compositions may also be formulated in rectal compositions such as suppositories or retention enemas, e.g., containing conventional suppository bases such as cocoa butter or other glycerides.

Pharmaceutical compositions may also be formulated in a way that allows for the sustained delivery of those compounds to a mammal for a period of several days, to at least several weeks, to a month or more. Such formulations are described, for example, in U.S. Pat. Nos. 5,968,895 and 6,180,608. Any pharmaceutically-acceptable, sustained-release formulation known in the art is contemplated.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols. Such carriers and excipients enable the pharmaceutical compositions to be formulated as tablets, pills, dragees, capsules, liquids, gels, syrups, slurries, suspensions and the like, for oral ingestion by a patient to be treated.

Some formulations are contemplated to comprise one or more coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added for identification or to characterize different combinations of active compound doses.

Some formulations may compromise the long-term stability of pharmaceutical composition. To enhance the stability of the pharmaceutical composition and extend its shelf life, the pharmaceutical composition may be lyophilized to a dry form for reconstitution before use with an appropriate sterile liquid. However, the loss of secondary, tertiary and quaternary structure of the peptide can occur during freezing and drying. Consequently, cryoprotectants may have to be included to maintain the structural integrity of the peptide during the lyophilization process. Suitable cryoprotectants include agarose, aldaric acids, alditols, aldonic acid, alginic acid, allose, altrose, amino sugars, amylopectin, amylose, arabinans, arabinose, ascorbic acid, carrageenan, cellulose, chitin, chondroitin, dermatan, dextran, erythrose, erythrulose, ethylene glycol, fructans, fructose, fucans, fucoidan, galactans, galactocarolose, galactosamine, galactose, galacturonans, galacturonic acid, glucans, glucaric acid, gluconic acid, glucosamine, glucose, glucuronic acid, glyceraldehyde, glycerol, glycoaldehyde, glycogen, gulose, heptose, hexose, hyaluronic acid, idose, inositol, isoascorbic acid, keratin, ketoses, lactone, lactose, levan, lyxose, maltose, mannans, mannitol, mannose, mannuronic acid, methyl $\alpha$-glucopyranoside, neuraminic acid, pectic acids, pectins, pentaerythritol, pentose, polyethylene glycol, polypropylene glycol, psicose, pullulan, pustulan, ribose, sorbitol, sorbose, starch, sucrose, tagatose, talose, threose, trehalose, uronic acid, xanthan gum, xylans, xylose and xylulose, and combinations thereof.

Therapeutic and Prophylactic Applications

In particular embodiments, methods are provided for treating or ameliorating HIV-mediated neurodegeneration and HIV-associated dementia (HAD) in a subject using Helix A gp120 peptides and pharmaceutical compositions comprising the same. The peptide or pharmaceutical composition is administered to a subject for a time and in an amount sufficient to reduce the level of neurodegeneration and/or dementia in the subject. In other embodiments, methods are provided for prophylactically treating or preventing HIV-mediated neurodegeneration and HIV-associated dementia (HAD) in a subject using Helix A gp120 peptides and pharmaceutical compositions comprising the same. The peptide or pharmaceutical composition is administered to a subject for a time and in an amount sufficient to delay the onset of neurodegeneration and/or dementia in the subject.

Effective dosages of the peptides may be determined through procedures well known to those in the art which address such parameters as biological half-life, bioavailability, and toxicity. Effective dosages may vary according to factors such as the disease state, age, and weight of the subject, and the ability of the compound to elicit a desired response in the subject. Dosage regimens can be adjusted to provide the optimum therapeutic response.

An effective dose refers to that amount of the peptide or pharmaceutical composition comprising the same that is sufficient to result in amelioration of symptoms or a prolongation of survival in a patient. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Peptides that exhibit large therapeutic indices are preferred.

The data obtained from cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any pharmaceutical composition used in any of the contemplated and disclosed methods, the therapeutically effective dose can be estimated initially from cell culture assays. A dose may be formulated in animal models to achieve a circulating plasma concentration range that includes the $IC_{50}$. Such information can be used to more accurately determine useful doses in humans. Levels in plasma may be measured, for example, by high performance liquid chromatography (HPLC).

EXAMPLES

The invention is now described with reference to the following Examples. These Examples are provided for the purpose of illustration only, and the invention is not limited to these Examples, but rather encompasses all variations which are evident as a result of the teachings provided herein.

Example 1

Protein Reagents: All gp120s and Tat were purchased from Immunodiagnostics Inc, Woburn, Mass. Human recombinant TUBB3 was obtained from MyBioSource, San Diego, Calif. Porcine tubulin dimer and assembled microtubules (containing ~25% of TUBB3) were purchased from Cytoskeleton Inc, Denver, Colo. Helix-A and -B and tubulin CTTs (<98% pure) were synthesized and purchased from GENSCRIPT®, Piscataway, N.J.

Dot blot analysis: CTTs or Helix-A and -B peptides (2 μg each) were spotted on a nitrocellulose membrane and allowed to dry. The membrane was then incubated in blocking buffer (5% BSA in TBST [150 nM NaCl, 20 mM Tris-base, pH 7.5, 0.05% TWEEN® 20]) for 2 hours followed by incubation with a solution composed of 5 μg recombinant gp120 (for binding to CTTs) or 5 μg recombinant TUBB3 (for Helix-A and -B) in 20 mL of TBST for 2 hours. The membranes were washed and then incubated with a mouse anti-gp120 antibody (1:1000; Immunodiagnostics, Inc.) or mouse anti-TUBB3 antibody (1:5000; Covance, N.J.) in TBST for 2 hours. Membranes were washed and incubated in goat anti-mouse HP-conjugated secondary antibody (1:20,000; Jackson ImmunoResearch Laboratories, Inc., PA). Visualization of the bands was then accomplished by the addition of PIERCE® SUPERSIGNAL™ West Pico-Stable Peroxidase Solution and Luminol/Enhancer Solution (Pierce Biotechnology, Inc., Rockford, Ill.).

Surface plasmon resonance (SPR). BIACORE® T200™ was used to determine the kinetic parameters for the binding of recombinant TUBB3, tubulin dimer, and assembled microtubules (ligands) to the various isoforms of gp120 or related peptides (analytes). Recombinant TUBB3, tubulin dimer, and assembled MTs were covalently attached to different flow cells of a carboxymethyldextran (CM5) sensor chip by amine coupling. The chip surface was activated for 720 sec at 10 μL/min with of 1:1 mixture of 0.1 M N-Hydroxysuccinimide (NHS) and 0.5 M 1-Ethyl-3-(-3-dimethylaminopropyl)-carbodiimide hydrochloride (EDC). Each ligand was diluted in 10 mM sodium acetate, pH 4.0 (final concentrations were 0.67 μg/mL for tubulin, 33.3 μg/mL for tubulin dimer, and 50 μg/mL for microtubules) and injected 280 sec for tubulin, 150 sec for tubulin dimer, and 1400 sec for microtubules at 10 μL/min flow rate. After ligand capture, the surfaces were deactivated by injecting 1 M ethanolamine for 720 sec at 10 μL/min. HBS-P (10 mM HEPES, pH7.4, 150 mM NaCl, 0.05% P-20) with 2 mM $MgCl_2$ used as the running buffer. Flow cell 1 on each chip was left empty and used for reference surface. TUBB3 (1040 RU), tubulin dimer (2086 RU), and assembled MTs (990 RU) were captured on the remaining 3 flow cells. Kinetic studies were performed by injecting different concentrations of the analytes in triplicate. The chip surface was regenerated by with 10 mM glycine pH 1.5 injected for 30 sec at a flow rate of 100 μL/min. Each sample was injected for 60 sec (contact time) followed by a dissociation time of 300 sec at a flow rate of 100 μL/min. Data was analyzed with BIACORE® T200™ Evaluation Software (version 1) to determine the equilibrium dissociation constant ($K_D$) from a 1:1 binding model. Binding studies with peptides Helix A and Helix B were done in the same way as described above. Kinetic studies were performed by injecting different concentrations (20 μM, 10 μM, 5 μM, 2.5 μM, 1.25 μM and 0.625 μM) of Helix A and Helix B. Competition experiments with Helix A and Helix B were performed by mixing 100 nM gp120 isoforms with 10 μM of each peptide and injecting over the sensorchip surface.

Synthesis and characterization of mesoporous silica nanoparticles: The materials have been purchased from the following sources: tetraethyl orthosilicate (TEOS), 3-(aminopropyl) triethoxysilane (APTES), hexadecyltrimethylammonium bromide (CTAB), 2-propanol (IPA), ethanol, HCl, 2-mercptoethanol (BME), and N-(3-diethylaminopropyl)-N'-ethylcarbodiimide hydrochloride (EDC) from SIGMA-ALDRICH® (St. Louis, Mo.); 2-ethylsulfonic acid (MES), and NaCl from Acros Organics (Fairlawn, N.J.); NH4F and N-hydroxysulfosuccinimide (Sulfo-NHS) from THERMO FISHER SCIENTIFIC® (Waltham, Mass.). A modified Stober reaction was used to synthesize MSNs. 162.909 mg ammonium fluoride and 144.87 mg CTAB were dissolved in 48.24 mL water (80° C. for 1 hour). 0.988 ml of TEOS was then added drop-wise to the solution and the reaction proceeded for 2 hours at 80° C. After two ethanol washes MSNs were let overnight in a 2% HCl in ethanol solution to remove surfactants. The particles were washed with 50% ethanol and stored in IPA. MSNs were modified with APTES in a solution of 2% APTES and 5% MILLIPORE® water by volume in IPA at a concentration of 1 mg nanoparticle/ml APTES solution. The modification took place at 35° C. for 2 hours under constant and vigorous agitation. MSNs-APTES were conjugated to Helix-A peptide via EDC/sulfo-NHS coupling reaction. The FITC-Helix-A peptide was activated in a solution of 2 mM EDC/5 mM sulfo-NHS in 0.1 M MES and 0.5 M NaCl for 15 minutes at 1 mg/mL. After peptide activation, BME was added at a concentration of 20 mM. 1 mg of MSN-APTES was dispersed in the reaction solution. The conjugation took place at room temperature for 2 hours under constant and vigorous agitation. Hydroxylamine HCl was added to the solution at a concentration of 10 mM to quench the reaction. Dynamic Light Scattering (DLS) and zeta ($\xi$)-potential characterization were performed using a ZETASIZER® ZEN3600 (MALVERN INSTRUMENTS®, Worcestershire, UK). For DLS, scattered light detection was measure at 90° to the incident beam (a 25 mW laser at 660 nm wavelength). For $\xi$-potential analysis the same parameters were used but scattered light was detected at 15°. The $\xi$-potential of MSN-APTES was positive (39.5 mV), and after the crosslink with the peptide (MSN-APTES-Helix-$\alpha$) decreased to 12.06 mV. Fourier Transformed Infrared Spectroscopy was performed by creating a pellet of 5% sample and 95% KBr (SIGMA-ALDRICH®) by volume and analyzing absorbance of the pellet on a Nicolet 6700 FT-IR Spectrometer (THERMO FISHER SCIENTIFIC®). The spectra were reported after background subtraction, baseline correction and binomial smoothing (11 points). The second derivatives were obtained by the Savitsky-Golay method (third grade polynomial, 5 smoothing points) using the OMNIC™ software.

Primary cortical neurons: Cortical neuronal cultures were prepared from the cortex of embryonic (E17-18) Sprague Dawley rats (Charles River, Mass.). Cells were seeded onto poly-L-lysine pre-coated plates in Neurobasal Medium containing 2% B27 supplement, 25 nM glutamate, 0.5 mM L-glutamine, and 1% antibiotic-antimycotic solution (INVITROGEN®, Carlsbad, Calif.). Cultures were grown at 37° C. in 5% $CO_2$/95% air for 7 days. Cultures contained ~5% of non-neuronal cells.

Liquid chomatography-mass spectrometry (LC-MS/MS): Neurons exposed to gp120IIIB were lysated in RIPA buffer with protease and phosphatase inhibitors (THERMO FISHER SCIENTIFIC®) at 4° C. and then incubated with mouse anti-gp120 antibody. Gp120 complex of interacting proteins was eluted from immobilized protein A beads, reduced, alkylated and digested with trypsin. The tryptic digests were analyzed by mass spectrometry, using a LTQ ORBITRAP XL™ hybrid FTMS (Fourier transform mass spectrometer) (THERMO FISHER SCIENTIFIC®). Peptide separation was performed with solvent A (0.1% HCOOH in $H_2O$) and solvent B (0.1% formic acid in ACN), using the following gradient: from 5% B for 1 minute to 60% B in 70 minutes. Peptides were analyzed using a precursor mass range of 300-5000 Da. MS/MS analyses were used to query a non-redundant protein database (rat.fasta) using the software SEQUEST™. The search was performed using trypsin as proteolytic enzyme, 2 max missed cleavage, S-carbamidomethylation of cysteine, a precursor mass tolerance of 30 ppm and a fragment mass tolerance of 0.1 Da, and rat as taxonomic origin of the samples.

Transmission electron microscopy: Primary cortical neurons were fixed in 3% glutaraldehyde, 2% paraformaldehyde in 0.1M cacodylate buffer, pH 7.3 and were washed in 0.1M cacodylate buffer and treated with 0.1% Millipore-filtered buffered tannic acid, post-fixed with 1% buffered osmium tetroxide for 30 min, and stained with 1% MILLIPORE®-filtered uranyl acetate. The samples were washed several times in water, then dehydrated in increasing concentrations of ethanol, infiltrated, and embedded in LX-112 medium. The samples were polymerized in a 60° C. oven for 2 days. Ultrathin sections were cut in a LEICA® Ultracut microtome (LEICA®, Deerfield, Ill.), stained with uranyl acetate and lead citrate in a LEICA® EM Stainer, and examined in a JEM 1010 transmission electron microscope (JEOL®, MA) at an accelerating voltage of 80 kV. Digital images were obtained using an AMT Imaging System (Advanced Microscopy Techniques Corp, Mass.).

Immunocytochemistry of primary neurons: Primary cortical neurons were maintained on glass coverslips for 7 days and fixed in 4% paraformaldehyde/phosphate buffer with 4% sucrose for 20 minutes at room temperature (RT). Fixed cells were blocked and permeabilized in 5% non-fat milk in TBS-T (150 nM NaCl, 20 mM Tris-base, pH 7.5, 0.1% TRITON™ X100) for 1 hour at RT. Cells were incubated overnight at 4° C. with mouse anti-MAP2 antibody (1:5000; SIGMA-ALDRICH®, MO) along or in combination with TOM20 (1:2000; Santa Cruz, Calif.). Coverslips were washed with PBS-T and correspondent fluorescence-conjugated secondary antibody (1:2000; INVITROGEN®, CA) were applied for 1 hour at RT. Coverslips were washed with TBS-T and mounted with Fluoro-Gel with TES buffer (Electron Microscopy Sciences, PA). Cells were imaged using an FV300 laser confocal scanning system attached to an OLYMPUS® IX-70 (Tokyo, Japan) upright microscope. Image scale was calibrated and length of MAP-2 positive processes was measured in 10 neurons per field using ImageJ.

Stochastic optical reconstruction microscopy (STORM): STORM was performed using a NIKON® A1 confocal microscope with CFI SR Apochromat TIRF 100× oil objective and ANDOR® IXON® 897 EMCCD camera. Primary cortical neurons were maintained on glass coverslips ($1\times10^5$/mL) for 7 days, then fixed with 3% PFA and 0.1% gluteraldehyde for 10 minutes, and reduced with 0.1% $NaBH_7$ for 7 minutes at RT. Cells were washed three times with 0.1% sodium cacodylate buffer, and blocking buffer (5% non-fat milk with 0.2% TRITON™) was applied for 20 minutes at RT. Rabbit anti-TOM20 (1:200; Santa Cruz, Calif.) and rat anti-tubulin (1:5000; ABCAM®, MA) were used overnight to label mitochondria and cytoskeleton, respectively. Correspondent fluorescence-conjugated secondary antibody (1:2,000; INVITROGEN®, CA) were applied for 1 hour at RT. Samples were post-fixed with the same initial fixation solution mentioned above, and coverslips were mounted using imaging buffer with cysteamine (MEA) and used immediately. Secondary fluorophores were bleached using 647 nm and 561 nm lasers until blinking was evident (1-3 minutes), followed by image recording. Mitochondrial shape and size was measured manually using NIKON® AR analysis software.

Cell viability: The viability of primary cortical neurons was estimated by HOECHST® 33258 and propidium iodide (HOECHST®/PI; SIGMA-ALDRICH®) co-staining and visualized using a fluorescence microscope OLYMPUS®

IX71. HOECHST®/PI-positive cells were then counted using Image) and expressed as a percentage of the total number of neurons.

Statistical analysis: Statistical analyses were performed using GraphPad Prism software (GraphPad Software, Inc.). Results are depicted as mean±standard error of mean. For a comparison of more than two groups, an ANOVA test, followed by a Bonferroni test for multiple comparisons, was applied. P values of <0.05 indicate statistical significance.

Example 2 gp120IIIB Interacts with the C-Terminal Tails (CTTs) of Tubulin Isoforms

Several CTTs (see Table 1) synthesized by GENSCRIPT® were used. Peptides (2 μg each) were spotted on a nitrocellulose membrane and incubated with a solution composed of 5 μg of gp120IIIB (Immunodiagnostics) in 20 mL of TBS-TWEEN® 2 hours at RT, followed by incubation with a specific primary antibody (Immunodiagnostics, +4° C., ON). Following incubation with a corresponding HRP-conjugated secondary antibody 1 hour at RT, the immunocomplexes were visualized with chemiluminescence.

TABLE 1

| Tubulin isoform | Distinctive feature | Sequence | Expression | Binding to gp120 |
|---|---|---|---|---|
| α1A/1B | tyrosinated isoform | $^{441}$EGEGEEEGEEY$^{451}$ (SEQ ID NO: 3) | widely expressed | NO |
| α1A/1B | detyrosinated isoform | $^{441}$EGEGEEEGEE$^{450}$ (SEQ ID NO: 4) | widely expressed; highly abundant in cancer epithelial cells | NO |
| α1A/1B | A2 isoform1 | $^{441}$EGEGEEEGE$^{449}$ (SEQ ID NO: 5) | present exclusively in neurons | YES |
| α1A/1B | more basic2 | $^{441}$EGEGEEEGQQ (SEQ ID NO: 6) | | NO |
| α1A/1B | more basic2 | $^{441}$EGEGEEEGQQQ (SEQ ID NO: 7) | | NO |
| α1A/1B | more basic2 | $^{441}$EGEGEEEGQQQQ (SEQ ID NO: 8) | | NO |
| α4 | tyrosinated isoform | $^{441}$EDEDEGEEY$^{449}$ (SEQ ID NO: 9) | widely expressed | NO |
| α4 | detyrosinated isoform | $^{441}$EDEDEGEE$^{448}$ (SEQ ID NO: 10) | widely expressed | NO |
| α4 | Δ2 isoform1 | $^{441}$EDEDEGE$^{448}$ (SEQ ID NO: 11) | widely expressed | NO |
| β2A/2B | | $^{437}$EEEEGEDEA$^{455}$ (SEQ ID NO: 12) | widely expressed; highly abundant in neurons | NO |
| β3 | | $^{438}$EDDEEESEA$^{446}$ (SEQ ID NO: 13) | expressed exclusively in neurons | NO |
| 1Δ2 isoform-irreversible derivative of detyrosination. by replacing two acidic E residues with Q residues (alters binding properties). | | | | YES |

CTTs of neuron-specific isoforms of tubulin β-3 (TUBB3) and tubulin-α1A/1B Δ2, were identified as potential binding partners for gp120IIIB

Example 3

Binding Affinity of gp120s to Tubulin

Recombinant TUBB3, tubulin dimer, and assembled MTs from bovine brains were immobilized on a BIACORE® CM5 chip by amine coupling. Different concentrations of gp120s (from 3.13 to 100 nM) were injected over the surface in triplicates in each experiment. The kinetics of interaction was analyzed using a BIACORE® T200™ instrument. BiaEvaluation software was used to calculate binding affinities based on 1:1 binding model. Results from two independent experiments are presented in Table 2.

TABLE 2

| Analyte | $K_D$(M) | U-value | Mean |
|---|---|---|---|
| | Ligand: TUBB3 | | |
| gp120IIIB | 7.91E−09 | 2 | 7.5 nM |
| | 7.05E−09 | 2 | |
| gp120ADA | 5.48E−09 | 3 | 10.3 nM |
| | 1.52E−08 | 2 | |
| gp120MN | 9.01E−07 | 12 | 740 nM |
| | 5.79E−07 | 15 | |
| | Ligand: Tubulin Dimer | | |
| gp120IIIB | 1.69E−09 | 2 | 12.3 nM |
| | 7.68E−09 | 4 | |
| gp120ADA | 5.40E−09 | 4 | 11.2 nM |
| | 1.71E−09 | 2 | |

TABLE 2-continued

| Analyte | $K_D$(M) | U-value | Mean |
|---|---|---|---|
| gp120MN | 6.51E−09 | 26 | 79.2 nM |
| | 9.33E−09 | 5 | |
| | Ligand: Assembled MTs | | |
| gp120IIIB | 1.16E−09 | 7 | 10.0 nM |
| | 8.46E−09 | 4 | |

TABLE 2-continued

| Analyte | $K_D$(M) | U-value | Mean |
|---|---|---|---|
| gp120ADA | 5.62E−09 | 5 | 12.0 nM |
| | 1.83E−09 | 3 | |
| gp120MN | 1.19E−09 | 7 | 62.7 nM |
| | 1.14E−09 | 7 | |

To examine specificity of this binding, binding to Tat was investigated. Tat is another viral protein that is endocytosed by neurons and causes synaptodendritic injury. SPR experiments showed that Tat had no specific binding to TUBB3, tubulin dimer or MTs.

Example 4

Tubulin β-3 Interacts with the Helices of gp120

In order to predict potential regions for gp120 to interact with tubulin, a homology search for other tubulin-binding proteins was performed. An overlay of their crystal structures suggested that one of the surface α-helices, conserved across all gp120 variants, might interact with tubulin. Using dot blot analysis, binding of Helix-A (NDMVEQMHEDIISLWDQSLK; SEQ ID NO: 1), but not Helix-B (RAKWNNTLKQIASK; SEQ ID NO: 14) to tubulin β-3, was verified.

Two α-helices, Helix-A (NDMVEQMHEDIISLWDQSLK; SEQ ID NO: 1) and Helix-B (RAKWNNTLKQIASK; SEQ ID NO: 14), were synthesized by GENSCRIPT®. Peptides (2 μg each) were spotted on a nitrocellulose membrane and incubated with a solution composed of 5 μg of tubulin β-3 (MyBioSource) in 20 mL of TBS-Tween 2 hours at RT, followed by incubation with a specific primary antibody (COVANCE®, +4° C., ON). Following incubation with a corresponding HRP-conjugated secondary antibody 1 hour at RT, the immunocomplexes were visualized with chemiluminescence (Fisher).

Example 5

Helix A gp120 prevents gp120IIIB from binding to tubulin β-3, the tubulin dimer, microtubules and gp120MN from binding to tubulin β-3

As shown in Tables 3-6, Helix A gp120 prevents gp120IIIB interactions with tubulin, thus interfering with gp120-related axonal degeneration and dendritic injury, two key pathological events that may account for the synapto-dendritic atrophy observed in HAD.

TABLE 3

| Injections (60 sec) | Fc2: Tubulin β-3 1092 RU (2-1) RU |
|---|---|
| 100 nM GP120IIIB | 35 |
| 100 nM GP120IIIB | 44 |
| 1 uM Helix A | 0.9 |
| 1 uM Helix A | 0.7 |
| 1 uM Helix B | 0.1 |
| 1 uM Helix B | 0.5 |
| 10 uM Helix A | 5 |
| 10 uM Helix A | 4.4 |
| 10 uM Helix B | 1.1 |
| 10 uM Helix B | 1.2 |
| 100 nM GP120IIIB + 1 uM Helix A | 30 |
| 100 nM GP120IIIB + 1 uM Helix A | 33.3 |
| 100 nM GP120IIIB + 1 uM Helix B | 33 |

TABLE 3-continued

| Injections (60 sec) | Fc2: Tubulin β-3 1092 RU (2-1) RU |
|---|---|
| 100 nM GP120IIIB + 10 uM Helix A | 10 |
| 100 nM GP120IIIB + 10 uM Helix A | 6.5 |
| 100 nM GP120IIIB | 35 |
| 100 nM GP120 + 10 uM Helix B | 34 |
| 100 nM GP120 + 10 uM Helix B | 32 |

TABLE 4

| Injections (60 sec) | Fc3: Tubulin Dimer 1900 RU (3-1) RU |
|---|---|
| 100 nM GP120IIIB | 14 |
| 100 nM GP120IIIB | 18.6 |
| 1 uM Helix A | 0.4 |
| 1 uM Helix A | 0.5 |
| 1 uM Helix B | 0.4 |
| 1 uM Helix B | 0.5 |
| 10 uM Helix A | 0.8 |
| 10 uM Helix A | N/B |
| 10 uM Helix B | N/B |
| 10 uM Helix B | 0.4 |
| 100 nM GP120IIIB + 1 uM Helix A | 17 |
| 100 nM GP120IIIB + 1 uM Helix A | 18.4 |
| 100 nM GP120IIIB + 1 uM Helix B | 18.5 |
| 100 nM GP120IIIB + 10 uM Helix A | 5 |
| 100 nM GP120IIIB + 10 uM Helix A | 3.5 |
| 100 nM GP120IIIB | 21 |
| 100 nM GP120 + 10 uM Helix B | 20 |
| 100 nM GP120 + 10 uM Helix B | 18 |

TABLE 5

| Injections (60 sec) | Fc4: Microtubules 970 RU (4-1) RU |
|---|---|
| 100 nM GP120IIIB | 15 |
| 100 nM GP120IIIB | 23.2 |
| 1 uM Helix A | N/B |
| 1 uM Helix A | N/B |
| 1 uM Helix B | N/B |
| 1 uM Helix B | N/B |
| 10 uM Helix A | 3.2 |
| 10 uM Helix A | 1.3 |
| 10 uM Helix B | 0.2 |
| 10 uM Helix B | 0.2 |
| 100 nM GP120IIIB + 1 uM Helix A | 15 |
| 100 nM GP120IIIB + 1 uM Helix A | 16.7 |
| 100 nM GP120IIIB + 1 uM Helix B | 16.5 |
| 100 nM GP120IIIB + 10 uM Helix A | 3.8 |
| 100 nM GP120IIIB + 10 uM Helix A | 2.7 |
| 100 nM GP120IIIB | 19 |
| 100 nM GP120 + 10 uM Helix B | 19 |
| 100 nM GP120 + 10 uM Helix B | 20 |

TABLE 6

| Injections (60 sec) | Fc2: Tubulin β-3 1092 RU (2-1) RU |
|---|---|
| 100 nM GP120MN | 9 |
| 100 nM GP120MN | 8.8 |
| 1 uM Helix A | 0.9 |
| 1 uM Helix A | 0.7 |
| 1 uM Helix B | 0.1 |
| 1 uM Helix B | 0.5 |
| 10 uM Helix A | 5 |

TABLE 6-continued

| Injections (60 sec) | Fc2: Tubulin β-3 1092 RU (2-1) RU |
|---|---|
| 10 uM Helix A | 4.4 |
| 10 uM Helix B | 1.1 |
| 10 uM Helix B | 1.2 |
| 100 nM DP-EN + 1 uM Helix A | 7 |
| 100 nM GP-MN + 1 uM Helix A | 7 |

Example 6

Helix-A Peptide Prevents gp120-Mediated Neuronal Injury

Figure 6:
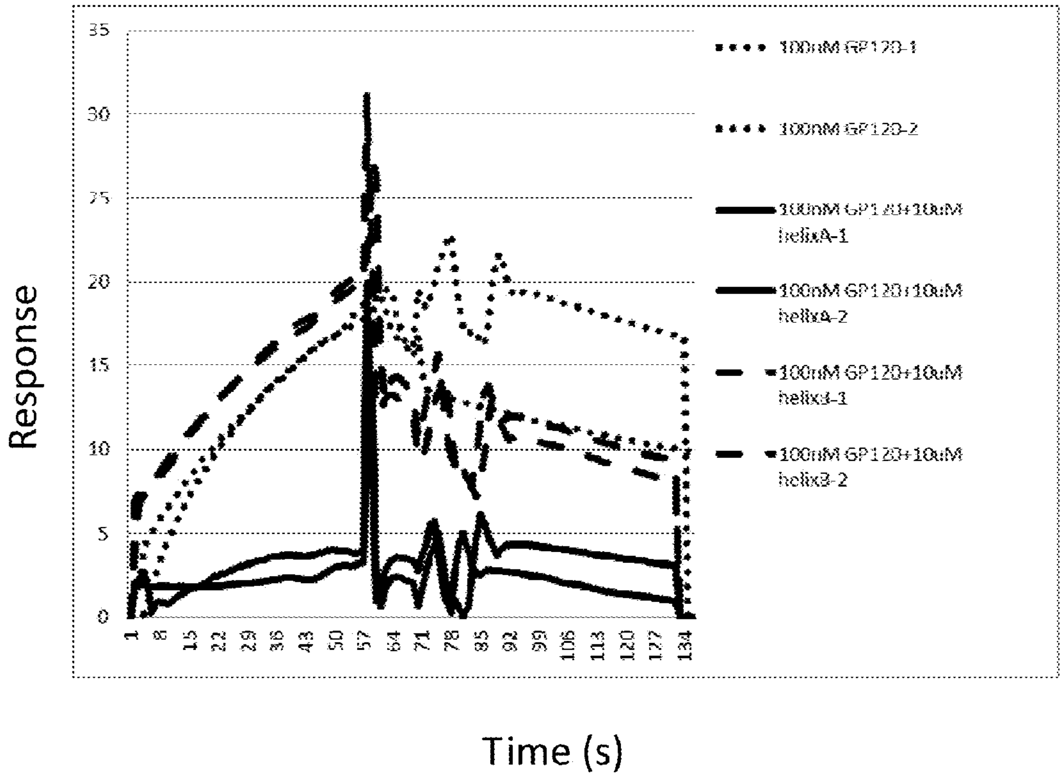
FIG. 6 shows that Helix A prevents gp120IIIB from binding to microtubules.
Figure 7:
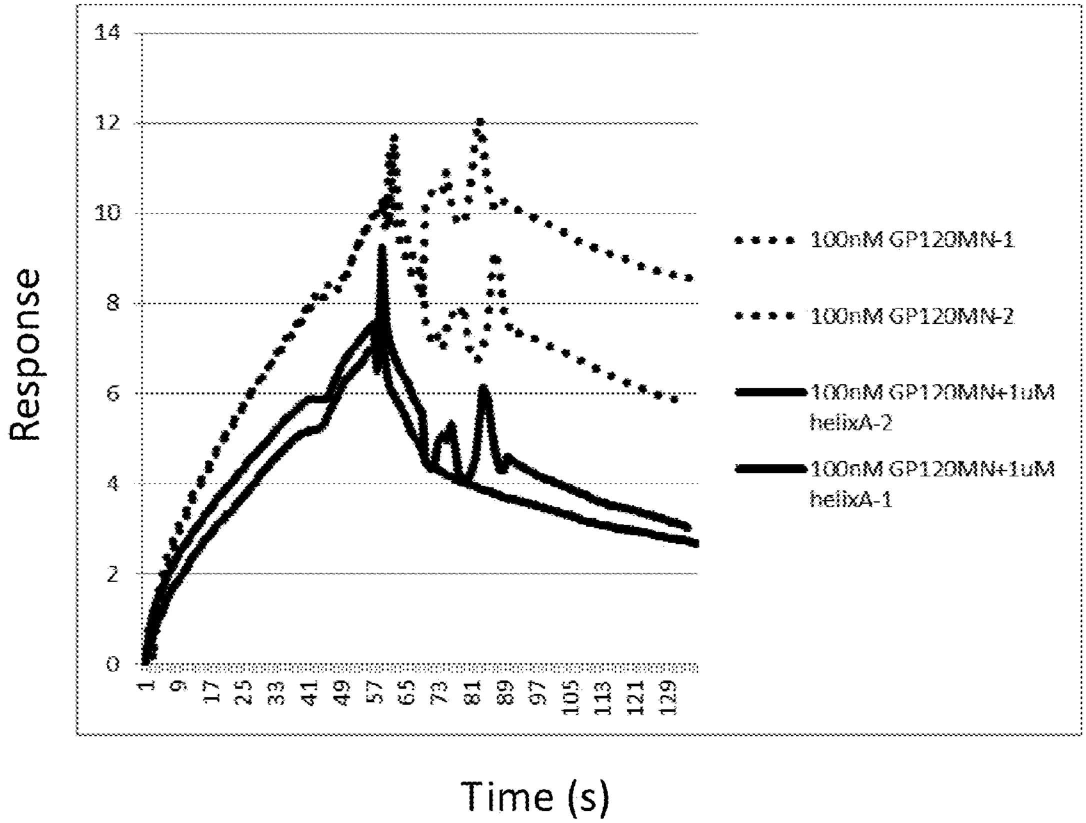
FIG. 7 shows that Helix A prevents gp120MN from binding to tubulin β-3.
Figure 8:
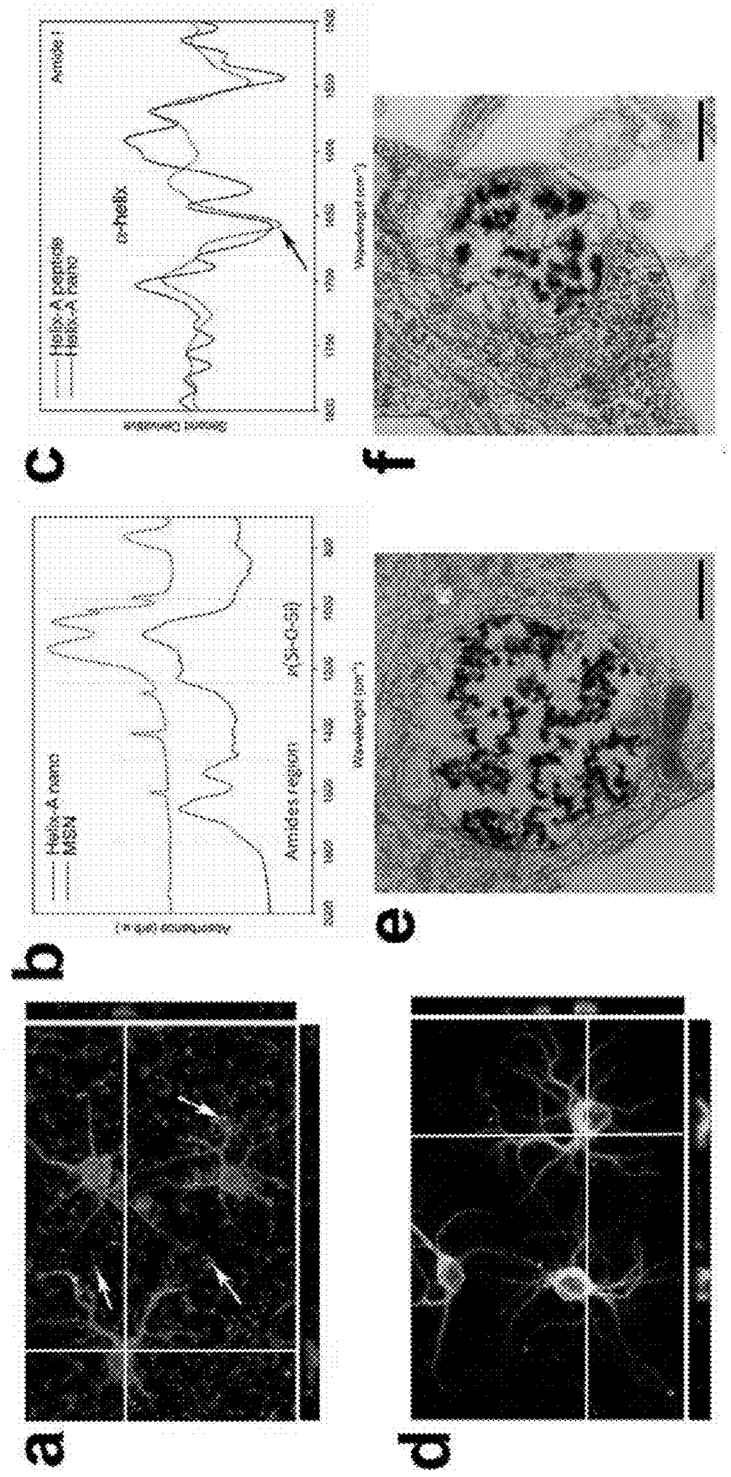
FIG. 8 shows that Helix-A nano (i.e., Helix A peptide crosslinked to mesoporous silica nanoparticles (MSN) modified with 3-(aminopropyl) triethoxysilane (APTES) crosses the neuronal membranes. a. Shown is a representative image (×60) of rat cortical neurons exposed for 24 hours to fluorescein 5(6)-isothiocyanate (FITC)-labeled Helix-A peptide (5 μM) and co-stained with the neuronal marker microtubule associated protein-2 (MAP-2, red). Neurons were optically sliced and a Z-stack was created using the Fluo View software. Arrows point at Helix-A peptide (green) outside cells, indicating that Helix-A peptide is not cell-membrane-penetrable. b. FTIR spectra of Helix-A nano. The gray line highlights the Amide region typical of peptide components. c. The second derivative of the Amide region shows the secondary structure of the Helix-A peptide that is mainly α-helix (arrow). d. Shown is a representative confocal image (×60) of cortical neurons exposed to Helix-A nano (5 μM) for 24 hours. The majority of green fluorescence is inside MAP-2 positive cells (green+red=yellow), indicating that Helix-A nano penetrates neuronal membranes. e and f. Representative images obtained by transmission electron microscopy showing unmodified MSN and Helix-A nano in intact and open lysosomes, respectively. Bar=500 nm.

The ability of the Helix-A peptide to prevent gp120 binding to MTs provide evidence that Helix-A peptides in accordance with the invention can provide a neuroprotective effect against gp120-mediated synaptic simplification and neurite pruning. The Helix-A peptide alone could not penetrate the cell membrane of primary cortical neurons (FIG. 8A). Therefore, it was crosslinked to mesoporous silica nanoparticles (MSN) modified with 3-(aminopropyl) triethoxysilane (APTES), to obtain Helix-A nano. The stability and the chemical features of Helix-A nano were determined by infrared spectroscopy (FTIR; FIG. 8B). The FTIR spectrum of Helix-A nano showed intense and broad peaks in the Amides region (1700-1500 $cm^{-1}$) that are a clear fingerprint of a high concentration of the peptide onto the MSN's surface. Moreover, second derivative analysis of the Amide I region (FIG. 8C) evidenced a band centered at 1656 $cm^{-1}$ confirming the stable α-helix secondary structure of the peptide. The Amide I band of Helix-A nano (FIG. 6B) displayed several components in the measured absorption spectra. In the second derivative spectra, the components that make up the Amide I band appear as well-resolved peaks in which the main absorption is still centered at 1656 $cm^{-1}$ (FIG. 6C) demonstrating that the structure of the peptide has not been modified during the synthesis process. Once bound on the MSN, Helix-A was evenly distributed across the neuronal cytosol (FIG. 6D). The intracellular localization of Helix-A nano was also confirmed by transmission electron microscopy imaging (FIGS. 8E and F).

Figure 9:
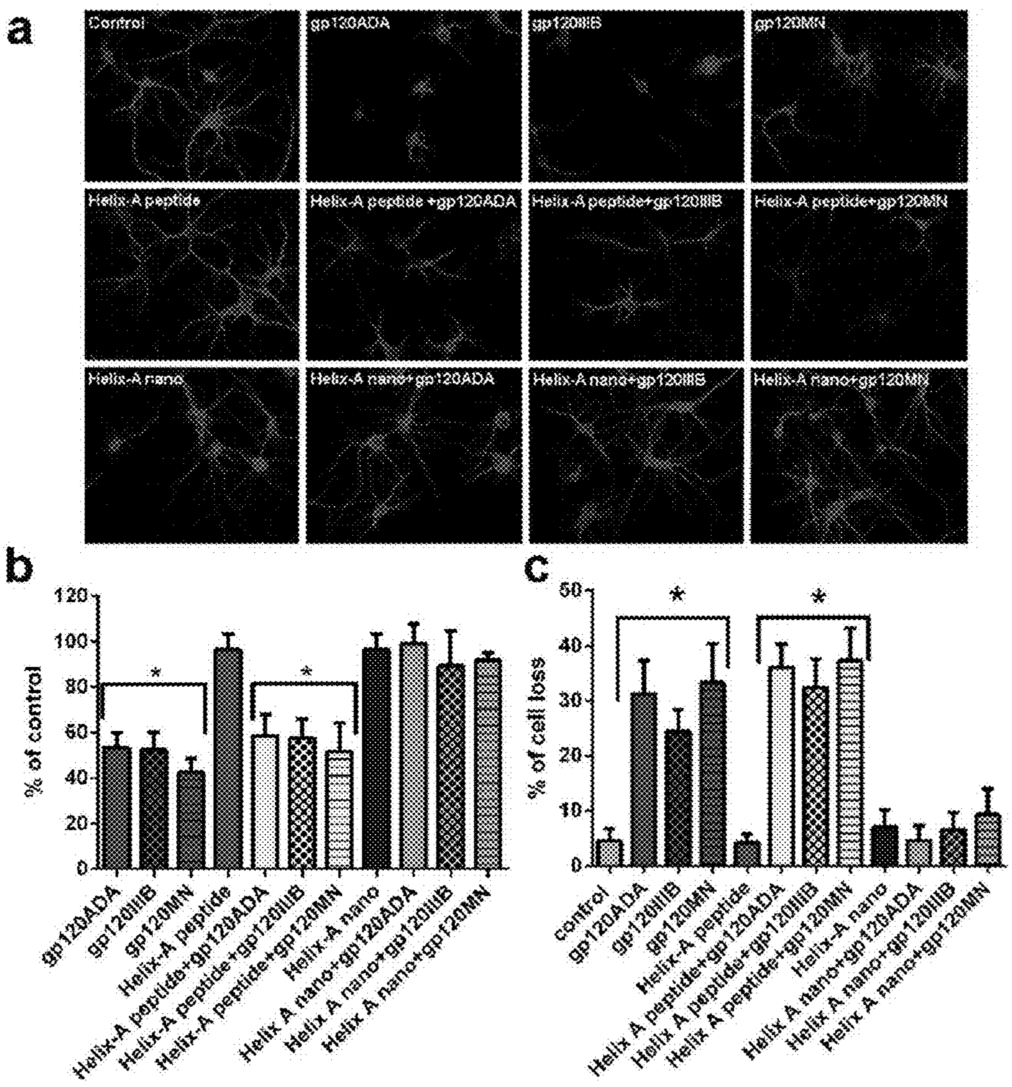
FIG. 9 shows that Helix-A nano blocks gp120-mediated synaptic simplification and cell death. a. Representative confocal images of cortical neurons exposed to boiled gp120 (control) or to the indicated gp120s (all 5 nM) alone or in combination with Helix-A peptide or Helix-A nano for 24 hours (5 μM each). Neurons were then fixed and stained for MAP-2 as described in Methods. b. Quantitative analysis of MAP-2 positive processes after various conditions confirming the neuroprotective effect of Helix-A nano. Data are the mean+SEM of three independent experiments (n=60 neurons per group per experiment) *p<0.01 vs control. c. Cell death was determined by HOECHST®/propidium iodide staining 24 hours after gp120s. Data are the mean+SEM of three separate experiments (n=200 neurons each group per experiment). *p<0.001 vs control. MSN alone did not prevent gp120-mediated neuronal cell death (data not shown). Helix-A nano blocked gp120-mediated cell death up to 96 h (data not shown).

To examine whether Helix-A nano was able to prevent gp120-induced neurotoxicity, rat cortical neurons were exposed to heat-inactivated gp120s (control) or to three different strains of gp120 alone or in combination with Helix-A peptide or Helix-A nano. Confocal microscopy of neuronal processes 24 h after treatments showed that Helix-A nano but not Helix-A peptide (FIG. 9A) prevented the gp120-mediated neurite pruning (FIG. 9B). In addition, Helix-A nano also blocked gp120-induced neuronal loss (FIG. 9C). Without wishing to be bound by theory, it is believed that Helix-A rescues neurons from axonal damage by preventing gp120 from binding to MTs.

Example 7 gp120 Alters Mitochondrial Distribution

Figure 10:
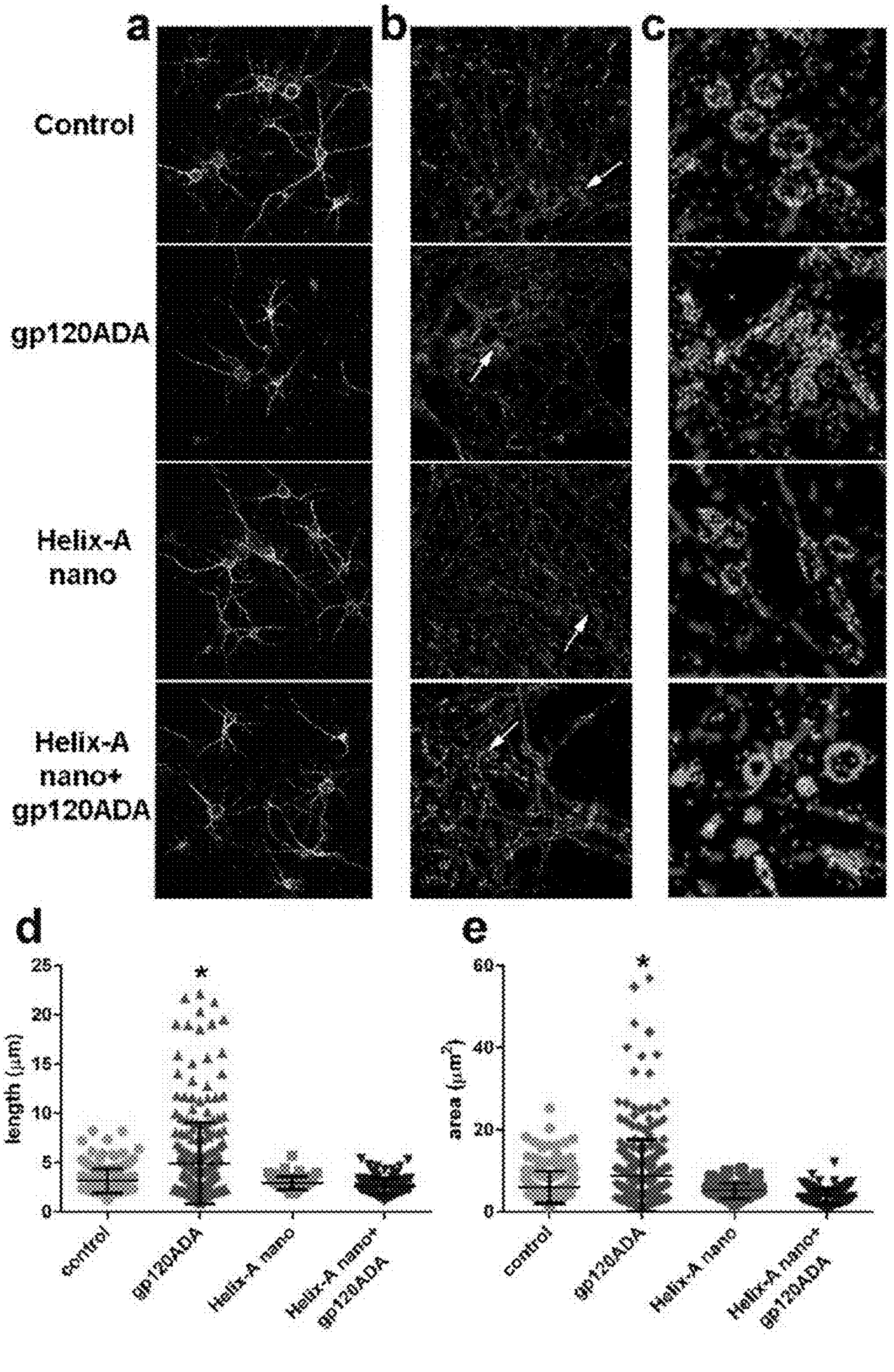
FIG. 10 shows that Helix-A nano prevents gp120-mediated elongation of mitochondria. a. Cortical neurons were exposed to boiled gp120 (control) or to the indicated stimuli for 24 hours. Cells were then fixed and co-stained for MAP-2 (red) and the mitochondrial outer membrane translocase complex, subunit TOM20 (green), and analyzed by confocal microscopy. Yellow (red+green) denotes overlapping of markers. b. Super resolution stochastic optical reconstruction microscopy (STORM) was used to visualize mitochondria aggregation and individual mitochondrion, and to quantify their size and distribution. Red=tubulin, green=TOM20. c. Enlargments of areas indicated by the arrows in b to show mitochondria morphology. d and e. The length (d) and area (e) of mitochondria were determined by analyzing STORM images (NIS-elements Advanced Research software, NIKON®, Japan). *p<0.01 vs control.
Figure 11:
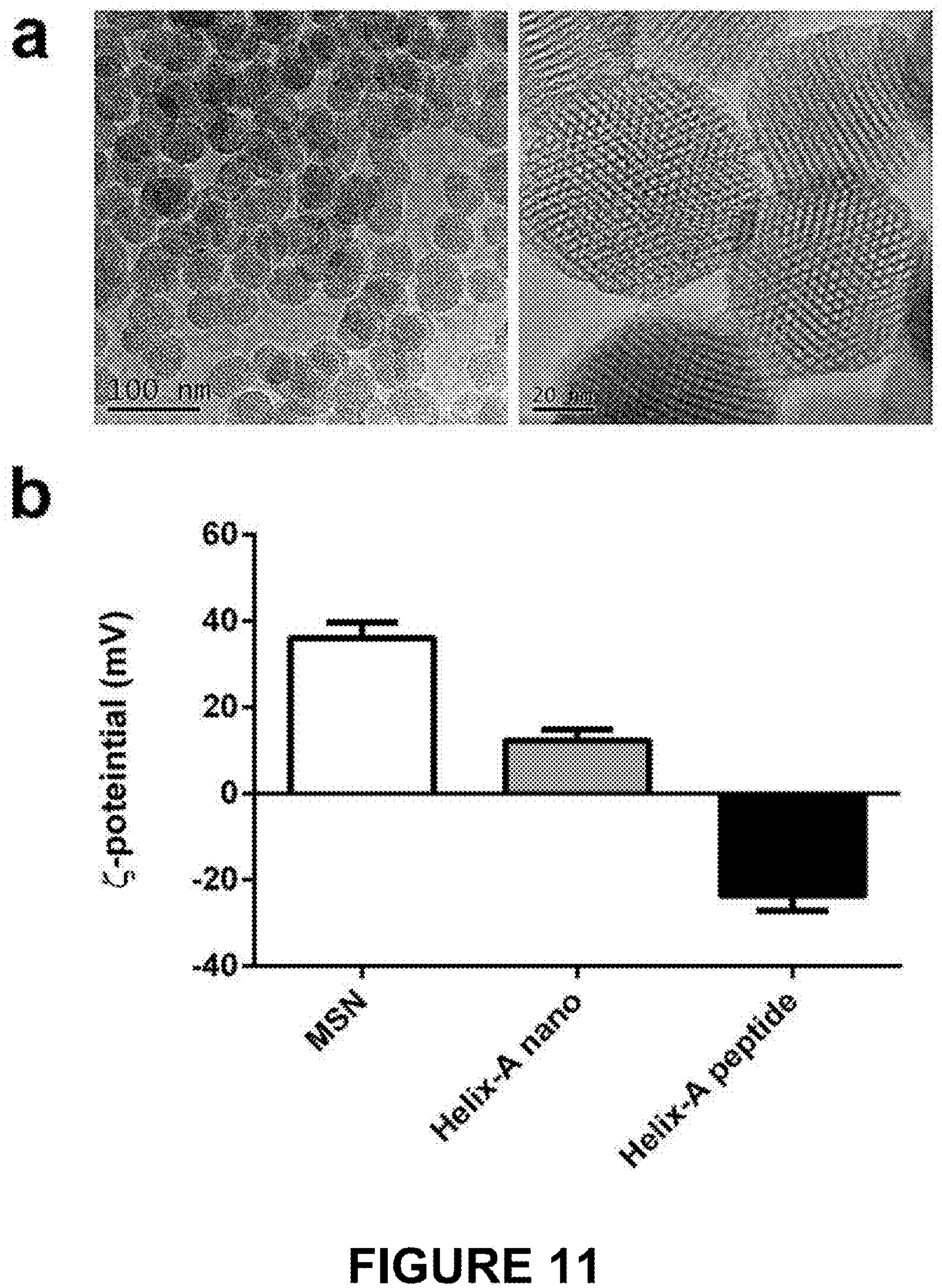
FIG. 11 shows the characteristics of silica nanoparticles. a. Examples of transmission electron microscopy of MSN synthesized via a co-condensation method. The images show the uniformity of the silica particles and their porosity. b. ξ-potential of MSN before and after the crosslinking with Helix-A peptide.

To investigate whether gp120 binding to MTs alters axonal transport of mitochondria, the effects of gp120 and Helix-A nano on mitochondrial distribution and size in primary cortical neurons was examined. Because the brain is infected predominantly by the M-tropic strain, neurons were exposed to gp120ADA. By 24 hours, neurons exposed to gp120ADA exhibited less mitochondria in processes (FIG. 10A). Such accumulation has been shown in several neurodegenerative diseases and it has been suggested to be the cause of synaptic injury. Moreover, neurons exposed to gp120 were detected because the neurons displayed mitochondria with morphological abnormalities manifested by their longer length (FIGS. 10B-D) and larger area (FIGS. 10B, C and E) which are consistent with mitochondrial damage. Helix-A nano (but not Helix-A) prevented the effects of gp120 on both somal accumulation of mitochondria (FIG. 10A) as well as their morphological abnormalities (FIGS. 10B-E). Since the observed effects of gp120 alone on mitochondria may account for neurotoxic actions of this viral protein, the protection elicited by the Helix-A peptide strongly suggests that the direct interaction of gp120 with TUBB3 is a crucial mechanism of gp120 neurotoxicity.

The disclosure of every patent, patent application, and publication cited herein is hereby incorporated herein by reference in its entirety. While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. A recombinant peptide comprising the sequence RQIKIWFQNRRMKWKKNDMVEQMHEDIISLWDQSLK (SEQ ID NO: 2).

2. The recombinant peptide according to claim 1, wherein the recombinant peptide is crosslinked to a 3-(aminopropyl) triethoxysilane (APTES)-modified silica particle.

3. The pharmaceutical composition comprising the recombinant peptide according to claim 2.

* * * * *